United States Patent [19]

Umezawa, deceased et al.

[11] Patent Number: 4,851,446

[45] Date of Patent: Jul. 25, 1989

[54] IMMUNOSUPPRESSING METHOD

[75] Inventors: Hamao Umezawa, deceased, late of Tokyo, by Kazuo Umezawa, executor; Tomio Takeuchi, Tokyo; Masaaki Ishizuka, Tokyo; Fuminori Abe, Tokyo; Akio Fujii, Kamakura; Teruya Nakamura, Kusatsu, all of Japan

[73] Assignee: Zaidan Hojin Biseibutsu Kagaku Kenkyu Kai, Tokyo, Japan

[21] Appl. No.: 22,409

[22] Filed: Mar. 6, 1987

Related U.S. Application Data

[63] Continuation-in-part of Ser. No. 793,279, Oct. 31, 1985, abandoned.

[30] Foreign Application Priority Data

Nov. 13, 1984 [JP] Japan .................................. 59-237480
Mar. 7, 1986 [JP] Japan .................................. 61-48475

[51] Int. Cl.$^4$ .................... A61K 31/16; A61K 31/165
[52] U.S. Cl. .................... 514/620; 514/626; 514/885
[58] Field of Search .................... 514/620, 626

[56] References Cited

U.S. PATENT DOCUMENTS 4,416,899 11/1983 Umezawa et al. .................. 514/626

OTHER PUBLICATIONS

Chemical Abstracts 99: 38063e (1983).

Primary Examiner—Leonard Schenkman
Attorney, Agent, or Firm—Henry C. Nields

[57] ABSTRACT

The present invention relates to an immunosuppressing method which comprises administering a spergualin-related compound represented by the following formula $$NH_2-\overset{NH}{\underset{\|}{C}}-NH-R_1-R_2-CONH-R_3-CONH-(CH_2)_4-$$
$$-NH-(CH_2)_3-NH$$

(wherein $R_1$ is $-(CH_2)_4-$, $-(CH_2)_6-$, $-\phenyl-CH_2-$, $-\phenyl-(CH_2)_2-$ of $-CH_2-\phenyl-$;

$R_2$ is $-(CH_2)_2-$ or $-CH=CH-$; and $R_3$ is $-\underset{OH}{\overset{|}{C}H}-$, $-\underset{OCH_3}{\overset{|}{C}H}-$, $-CH_2-$ or $-\underset{CH_2OH}{\overset{|}{C}H}-$ )

or pharmacologically acceptable salts thereof in an effective amount to a warm-blood animal.

5 Claims, No Drawings

IMMUNOSUPPRESSING METHOD

This application is a continuation-in-part of application Ser. No. 793,279, filed Oct. 31, 1985, now abandoned.

BACKGROUND OF THE INVENTION

A number of drugs with immunosuppressive actions have been known and they include alkylating agents, antimetabolites, antibiotics, steroids, folic acid antagonists and plant alkaloids.

Spergualin is a compound that was isolated by Umezawa, one of the inventors of the present invention, and others from the filtrate of a culture broth of Spergualin-producing microorganism of the genus Bacillus. The structural formula of Spergualin is shown below:

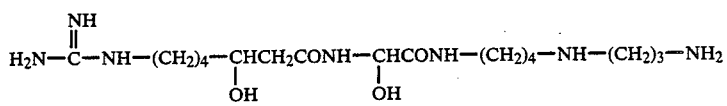

Spergualin is not only effective against mouse leukemia L-1210, mouse leukemia EL-4, Ehrlich carcinoma and sarcoma 180 but also holds promise as an agent to control malignant tumors (U.S. Pat. No. 4,416,899).

Umezawa et al. continued their studies on Spergualin compounds and have synthesized numerous Spergualin compounds which are stabler and have a stronger antitumor activity (BP No. 2111480A, EP No. 105193A).

The immunosuppressive effects of steroids are considered to be accomplished principally through the anti-inflammatory action and the lysis of lymphocytes. However, as is well known, steroids have diversified pharmacologic effects and cause many side effects. The other immunosuppressants are classified as "cytotoxic" substances and their action is directed, among other things, to the pathways of nucleic acid synthesis and may often cause serious side effects on hematopoietic organs. It is therefore desired to develop immunosuppressive drugs that act selectively on lymphocytes and other cells of immunological importance while causing minimum side effects.

DETAILED DESCRIPTION OF THE INVENTION

The present invention relates to immunosuppressing methods which comprises administrating a Spergualin-related compounds of formula (I) shown below (such compounds are hereinafter simply referred to as the compounds of the present invention):

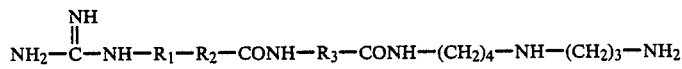 (I)

(wherein $R_1$ is $-(CH_2)_4-$, $-(CH_2)_6-$,

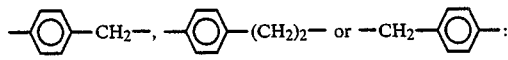

$R_2$ is $-(CH_2)_2-$ or $-CH=CH-$; and $R^3$ is

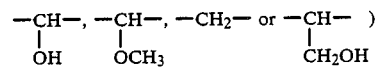

or pharmacologicaly acceptable salts thereof in an effective amount to a warm-blood animal for example, one having an autoimmune disease or being transplanted organs or skin.

The warm-blood animal in the present invention includes human.

Preferred compounds as the active ingredient are those wherein $R_1$ is $-(CH_2)_4-$ or $-(CH_2)_6-$; $R_2$ is $-(CH_2)_2-$; and $R_3$ is

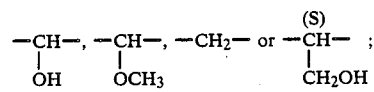

those wherein $R_1$ is

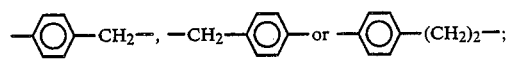

$R_2$ is $-(CH_2)_2-$; and $R_3$ is $-CH_2-$ or

and those wherein $R_1$ is $-(CH_2)_4-$ or $-(CH_2)_6-$; $R_2$ is $-CH=CH-$ (trans); and $R_3$ is

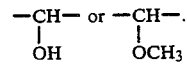

Specific examples of the compounds usable as the active ingredient of the immunosuppressive agent in accordance with the present invention are listed below:
(1) N-[4-(3-aminopropyl)aminobutyl]-2-(7-guanidinoheptanamido)-2-hydroxyethanamide;
(2) N-[4-(3-aminopropyl)aminobutyl]-2-(7-guanidinoheptanamino)-2-methoxyethanamide;
(3) N-[4-(3-aminopropyl)aminobutyl]-2-(9-guanidinononanamido)-2-hydroxyethanamide;
(4) N-[4-(3-aminopropyl)aminobutyl]-2-(7-guanidinoheptanamido)ethanamide;
(5) N-[4-(3-aminopropyl)aminobutyl]-2-(7-guanidinoheptanamido)-(S)-2-hydroxymethylethanamide;
(6) N-[4-(3-aminopropyl)aminobutyl]-2-4-(p-guanidinophenyl)butanamido]ethanamide;

(7) N-[4-(3-aminopropyl)aminobutyl]-2-[4-(p-guanidinophenyl)butanamido]-(S)-2-hydroxymethylethanamide;
(8) N-[4-(3-aminopropyl)aminobutyl]-2-[3-(p-guanidinomethylphenyl)propanamido]-(S)-2-hydroxymethylethanamide;
(9) N-[4-(3-aminopropyl)aminobutyl]-2-[5-(p-guanidinophenyl)pentanamido]-(S)-2-hydroxymethylethanamide;
(10) N-[4-(3-aminopropyl)aminobutyl]-2-[7-guanidinohepta-2-enamido]-2-methoxyethanamide; and
(11) N-[4-(3-aminopropyl)aminobutyl]-2-[9-guanidinonona-2-enamido]-2-hydroxyethanamide.

These compounds have the structures shown in Table 1.

The compounds of formula (I) may form salts with acids. Salt-forming acids may be inorganic or organic if they are pharmacologically acceptable. Preferred inorganic acids are hydrochloric acid, sulfuric acid, nitric acid and phosphoric acid; preferred organic acids include acetic acid, propionic acid, succinic acid, fumaric acid, maleic acid, malic acid, tartaric acid, glutaric acid, citric acid, benzenesulfonic acid, toluenesulfonic acid, methanesulfonic acid, ethanesulfonic acid, propanesulfonic acid, aspartic acid and glutamic acid.

Among the compounds listed above, (1) to (3) are known and described in BP 2111480A; compounds (4) and (5) are also known and described in EP 105193A; compounds (10) and (11) are also known and described in BP 2111480A. These known compounds may be

TABLE 1

Chemical Structures of Typical Examples of the Compounds of the Present Invention $$NH_2-\underset{\underset{NH}{\|}}{C}-NH-R_1-R_2-CONH-R_3CONH-(CH_2)_4-NH-(CH_2)_3-NH$$

| Compound No. | $R_1$ | $R_2$ | $R_3$ |
|---|---|---|---|
| (1) | $-(CH_2)_4-$ | $-(CH_2)_2-$ | $-CH(OH)-$ |
| (2) | $-(CH_2)_4-$ | $-(CH_2)_2-$ | $-CH(OCH_3)-$ |
| (3) | $-(CH_2)_6-$ | $-(CH_2)_2-$ | $-CH(OH)-$ |
| (4) | $-(CH_2)_4-$ | $-(CH_2)_2-$ | $-CH_2-$ |
| (5) | $-(CH_2)_4-$ | $-(CH_2)_2-$ | (S) $-CH(CH_2OH)-$ |
| (6) | $-C_6H_4-CH_2-$ | $-(CH_2)_2-$ | $-CH_2-$ |
| (7) | $-C_6H_4-CH_2-$ | $-(CH_2)_2-$ | (S) $-CH(CH_2OH)-$ |
| (8) | $-CH_2-C_6H_4-$ | $-(CH_2)_2-$ | (S) $-CH(CH_2OH)-$ |
| (9) | $-C_6H_4-(CH_2)_2-$ | $-(CH_2)_2-$ | (S) $-CH(CH_2OH)-$ |
| (10) | $-(CH_2)_4-$ | $-CH=CH-$ (trans) | $-CH(OCH_3)-$ |
| (11) | $-(CH_2)_6-$ | $-CH=CH-$ (trans) | $-CH(OH)-$ | synthesized by known methods. Compounds (6), (7), (8) and (9) are novel.

When the compounds of the said formula (I) are used as immunosuppressants, they are administered either independently or in admixture with excipients or carriers to form injections, oral formulations or suppositories. Pharmaceutically acceptable excipients and carriers should be selected and their type and composition are determined by the route and method administration. Illustrative liquid carriers include water, alcohols, as well as animal, vegetable and synthetic oils such as soybean oil, peanut oil, sesame oil and mineral oils. Exemplary solid carriers include sugars such as maltose and sucrose, amino acids, cellulose derivatives such as hydroxypropyl cellulose, and organic acid salts such as magnesium stearate. Carriers suitable for use in preparing injections include physiological saline, buffer solutions, solutions of sugars such as glucose, inositol, and mannitol, and glycols such as ethylene glycol, propylene glycol and poly(ethylene glycol). Alternatively, the compounds of the present invention may be freeze-dried together with excipients such as sugars (e.g. inositol, mannitol, glucose, mannose, maltose and sucrose) and amino acids (e.g. phenylalanine). Before intravenous injection, such freeze-dried compounds are dissolved in suitable solvents such as sterilized water, physiological saline, glucose solution, electrolyte solution and amino acid solution. The content of the compounds of the present invention in the immunosuppressive agent varies with the specific type of formulation, and it generally ranges from 0.1 to 100 wt%, preferably from 1 to 98 wt%. With injections, the content of the active ingredient generally ranges from 0.1 to 30 wt%, preferably from 1 to 10 wt%. For oral administration, the compounds of the present invention may be mixed with any of the solid or liquid carriers listed above, and used in the form of tablets, capsules, powders, granules, liquids or dry syrups. With capsules, tablets, granules and powders, the content of the active ingredient ranges generally from 5 to 100 wt%, preferably from 25 to 98 wt%.

The dosage of the immunosuppressant containing the compounds of the present invention as the active ingredient should be properly determined depending upon the age and body weight of the patient, as well as the severity and type of the disease. The effective dose generally ranges from 1 to 100 mg/kg·day for parenteral administration, and from 5 to 500 mg/kg·day for oral administration.

The compounds of the present invention are characterized by relatively low toxicity and small accumulation of toxicity upon continuous administration. The $LD_{50}$s of compounds (1) to (11) for a single intraperitoneal administration to mice are shown in Table 2.

TABLE 2

| Compound No. | Toxicity to mice $LD_{50}$ (mg/kg) |
| --- | --- |
| (1) | 25–50 |
| (2) | 12.5–25 |
| (3) | 12.5–25 |
| (4) | 12.5–25 |
| (5) | 12.5–25 |
| (6) | 25–50 |
| (7) | 25–50 |
| (8) | 25–50 |
| (9) | 25–50 |
| (10) | 25–50 |
| (11) | 25–50 |

TABLE 2-continued

| Compound No. | Toxicity to mice $LD_{50}$ (mg/kg) |
| --- | --- |
| (11) | 25–50 |

ACTION

The compounds of the present invention exert inhibitory effects on the function or proliferations of lymphocytes of immunological importance. Tests by the method of Waithe, et al. (Waithe, et al., Handbook of Experimental Immunology, page 26.1, 1978) revealed that the compounds of the present invention appreciably inhibited the T-lymphocyte blastogenesis stimulated by concanavalin A (Con A) and the reaction of B-lymphocyte blastogenesis stimulated by lipopolysaccharide (LPS). The present inventors therefore conducted in vivo experiments to examine the effects of the compounds of the present invention on T-lymphocytes. First, in accordance with the method of Lagrange et al. (Lagrange et al., Journal of Experimental Medicine, 139, 528–542, 1974), the compounds of the present inventin were examined for their effects on delayed-type hypersensitivity in mice that had been sensitized with sheep red blood cells. The delayed-type hypersensitivity could be blocked by administering the compounds for three consecutive days following the sensitization with sheep red blood cells. Additionally, in accordance with the method of Jerne et al. (Jerne et al., Cell-bound Antibodies, pp. 109–122, 1963), the compounds of the present invention were checked for their effects on the plaque-forming ability of spleen cells from mice sensitized by antigenic sheep red blood cells. The compounds of the present invention also exhibited blocking effects in this test. It was therefore confirmed that the compounds of the present invention exhibited inhibitory action on the antibody production by B-lymphocytes.

The above data show the ability of the compounds of the present invention to inhibit the functions of B- and T-lymphocytes. The inhibited B- and T-lymphocytes respectively mean the suppression of humoral immunity and that of cell-mediated immunity. Therefore, the immunosuppressants containing the compounds of the present invention as the active ingredient will prove very effective in suppressing tissue rejection that accompanies the transplantation of an organ or skin probably because of an abnormally enhanced humoral or cellular immunity. The compounds are also expected to be useful in the treatment of diseases caused primarily by various forms of autoimmunity such as systemic lupus erythematosus (SLE) aplastic anemia, hemolytic anemia, multiple sclerosis, myasthenia gravis (MG), insulin-dependent diabetes mellitus and rheumatoid arthritis and allergic disease. The compounds of the present invention seem to have a different mechanism of action than the prior art immunosuppressants and are believed to have no such serious side effects as causing disorder in hematopoietic organs as is caused by all immunosuppressants classified as cytotoxic substances, or the development of gastric ulcers and cataracts that often accompanies the administration of steroid hormones.

The following test results are provided for further illustrations of the pharmacologic effects of the compounds of the present invention.

TEST EXAMPLE 1

Inhibition of Delayed-Type Hypersensitivity in Mice Sensitized by Sheep Red Blood Cells CDF1 mice (8-wk-old, female) were sensitized by intravenous injection of $1 \times 10^5$ sheep red blood cells. Four days later, the sensitized mice were subcutaneously injected in one footpad with $1 \times 10^8$ sheep red blood cells so as to induce delayed-type hypersensitivity. The swelling of the footpad was measured at the 24th hour with a micrometer. Each of the test compounds was administered intraperitoneally in the amounts (mg/kg) indicated in Table 3 for a period of 3 days that started on the day following the initial sensitization. The degree of footpad swelling was indicated in relative values, with the value for a control given physiological saline instead of the test compounds being taken as 100%. The results are shown in Table 3, from which one can see the great ability of the compounds of the present invention to inhibit delayed type hypersensitivity.

TABLE 3

| Compound No. | Inhibition of Delayed Type Hypersensitivity Footpad swelling (%) | | | | | | | |
|---|---|---|---|---|---|---|---|---|
| | 0.20 | 0.39 | 0.78 | 1.56 | 3.13 | 6.25 | 12.5 | 25 |
| (1) | 72 | | 87 | | 29 | | 15 | |
| (2) | 99 | | 49 | | 5.5 | | | |
| (3) | 55 | | 32 | | 11 | | 6.6 | |
| (4) | | 99 | 111 | | | 46 | | |
| (5) | 81 | | 117 | | 58 | | | |
| (6) | | | | | | 102 | | 33 |
| (7) | | | | | | 54 | | 42 |
| (8) | | | | | 50 | 20 | | |
| (9) | | | | | 45 | 52 | | |
| (10) | | | | | 37 | 6.0 | | |
| (11) | | | | | 40 | 8.5 | | |
| Spergualin | | | | | 106 | 28 | | |
| Control (physiological saline) | 100 | 100* | 100 | 100 | 100 | 100 | 100 | 100 |

TEST EXAMPLE 2

Inhibition of Con A induced reaction of T-lymphocyte blastogenesis

Spleen cells from BALB/C mice were distributed among wells in a microplate so that each well contained $2 \times 10^5$ cells/0.2 ml. Each of the selected test compounds was added to all wells but one, the latter being used as a control. Con A (5 μg/ml) was added to all the wells and the so prepared cell suspensions were cultivated in a 5% $CO_2$ incubator for 72 hours at 37° C. Eight hours before the completion of the incubation, 1 uCi of $^3H$-thymidine was added to each well and the uptake of the thymidine by the cultured cells was measured with a liquid scintillation counter to estimate the progress of reaction of T-lymphocyte blastogenesis. The percentage inhibition of the mitogenesis by each of the test compounds was calculated by: $(1 - \text{Bdpm}/\text{Adpm}) \times 100$ wherein Adpm indicates the uptake count for the addition of Con A alone and Bdpm, the count for the addition of both Con A and the test compound. The results are shown in Table 4.

TABLE 4

| | Inhibition of Con A-induced reaction of T-lymphocyte blastogenesis | |
|---|---|---|
| | Inhibition, % | |
| Test Compound No. | 10 μg/ml | 100 μg/ml |
| (1) | 93 | 100 |
| (4) | 99 | 100 |
| (5) | 96 | 100 |
| (6) | 99 | 100 |
| (8) | 79 | 100 |
| (11) | 88 | 100 |
| Control (no compound added) | 0 | 0 |

As Table 4 shows, test compound Nos. 1, 4, 5, 6, 8 and 11 in accordance with the present invention exhibited a strong ability to inhibit the reaction of T-lymphocyte blastogenesis.

TEST EXAMPLE 3

Inhibition of LPS induced reaction of B-lymphocyte blastogenesis

The uptake of $^3H$-thymidine by B-cell was measured in accordance with the method used in Test Example 2, except that the inducer Con A was replaced by 100 μg/ml of LPS from *E. coli*. The percentage inhibition of blastogenesis by selected test compounds was also determined by the same method as used in Test Example 2. The results are shown in Table 5, from which one can see that compound Nos. 1, 4, 5, 6 and 11 of the present invention were highly effective in suppressing the LPS-induced B-lymphocyte blastogenesis.

TABLE 5

| | Inhibition of LPS-induced B-lymphocyte blastogenesis | |
|---|---|---|
| | Inhibition, % | |
| Test Compound No. | 10 μg/ml | 100 μg/ml |
| (1) | 98 | 100 |
| (4) | 100 | 100 |
| (5) | 88 | 100 |
| (6) | 96 | 100 |
| (11) | 98 | 100 |
| Control (no compound added) | 0 | 0 |

TEST EXAMPLE 4

Inhibition of Production of Antibody against Sheep Red Blood Cells

CDF1 mice (6-10 wk old, female) were immunized by intravenous injection of $1 \times 10^8$ sheep red blood cells. The mice were intraperitoneally administered 12.5 mg/kg·day of selected test compounds for a period of 3 days starting from the day following the intravenous injection. Four days later, spleen cells were isolated from the mice and the number of plaque-forming cells was counted. The percentage inhibition of antibody production was calculated by $(1 - B/A) \times 100$ wherein A is the count for a control group (given physiological saline) and B, for the treated group. Compounds Nos. 1, 2, 4, 5 and 6 exhibited inhibitions of 98.5%, 95.9%, 89.4%, 89.4% and 92.9%, respectively.

TEST EXAMPLE 5

The effect on skin graft was examined by the method described by DENHAM et al.(*) except that the Hooded and Wistar rats were replaced with SHR and Fischer (F344) rats. The results are shown in Table 6.

(*)DENHAM, S.; J. M. STYLES, R. K. BARFOOT & C. J. DEAN: Reversible suppression of allo-antibody production by cyclosporin A. Int. Archs. Allergy Appl. Immun. 62: 443-458, 1980

Table 6

| Compound No. | Survival Time of Skin Allografts in Rats by SGL-Derivatives Dose (mg/kg) | | | |
|---|---|---|---|---|
| | 0 | 3.13 | 6.25 | 12.5 |
| 1 | 6.5 ± 1.3 | 8.0 ± 1.2 | 11.1 ± 5.0 | 16.8 ± 1.9 |
| 2 | 5.8 ± 1.0 | 9.3 ± 1.5 | 14.9 ± 1.4 | 15.0 ± 4.0 |
| 7 | 6.4 ± 1.1 | 8.7 ± 1.0 | 12.4 ± 3.5 | 13.4 ± 5.1 |

The following Test Examples will be given to show therapeutic effects of the compound of the present invention on systemic lupus erythematosus and a model of aplastic anemia of mice.

TEST EXAMPLE 6

Therapeutic effect on systemic lupus erythematosus of mice (a spontaneous model considered to be closely similar to human systemic lupus erythematosus)

Method:

Male MRL/MpJ-lpr/lpr mice aged seven weeks were used. The mice were divided into groups each having ten animals and 8 mg/kg of compound No. 1 was intraperitoneally administered to each animal every day f0r 14 days. Separately, a raw feed was given to the control group. 15 and 25 days after the initiation of the administration, the animals were killed to weigh the lymphatic organs including the thymus, spleen and axillary lymph nodes of each animal and determine the antiDNA antibody titer in the serum thereof. The antiDNA antibody titer was determined by enzyme immunoassay (cf. Notes 1 and 2 below). The weight of each organ is expressed in terms of the specific body weight, i.e. (organ weight (g)/body weight (g))×100.

Results:

Tables 7 and 8 show the obtained results. Namely, the tumescence of each lymphatic organ was significantly suppressed by administering the compound No. 1 to the animals. Further the antiDNA antibody titer in the serum was significantly lowered thereby. These results suggest that the compound No. 1 would be effective in improving lupus diseases such as systemic lupus erythematosus.

TABLE 7

| | Effect on changes in the weights of various lymphatic organs | | | |
|---|---|---|---|---|
| | Weight (specific body weight, %) | | | |
| | 15th day | | 25 day | |
| Organ | Control | Compound No. 1 | Control | Compound No. 1 |
| thymus | 0.21 ± 0.05 | 0.05 ± 0.01* | 0.17 ± 0.03 | 0.09 ± 0.03* |
| spleen | 0.39 ± 0.07 | 0.23 ± 0.03* | 0.72 ± 0.10 | 0.41 ± 0.04* |
| axillary lymth nodes | 0.01 ± 0.03 | 0.07 ± 0.02* | 0.17 ± 0.06 | 0.07 ± 0.02* |

*p < 0.01

TABLE 8

| Effect on changes in the antiDNA antibody titers in serum | | |
|---|---|---|
| Days after administration | AntiDNA antibody titer (A045 ± S.D.) | |
| | Control | Compound No. 1 |
| 15 | 0.225 ± 0.106 | 0.145 ± 0.032* |
| 25 | 0.427 ± 0.119 | 0.252 ± 0.077** |

*p < 0.05; and
**p < 0.01
Note:
1. R. B. Eaton et al., Arthritis Rheum. 21, 52-62 (1983); and
2. D. G. Godfrey et al., J. Clin. Lab. Immunol. 15, 223-225 (1984).

TEST EXAMPLE 7

Therapeutic effect on immunointermediated aplastic anemia of mice

Method: $1 \times 10^7$ lymph node cells of a female CBA mouse aged ten weeks were intravenously injected to female C3H mice aged ten weeks which had been irradiated with X-ray all over the body to thereby induce aplastic anemia. From the next day of the irradiation, 1.56 mg/kg and 3.13 mg/kg of the compound No. 1 was intraperitoneally administered to the animals every day for ten days. Separately, a raw feed was given to the control group.

Results:

Table 9 shows the results. Namely, therapeutic effects of the administration of the compound No. 1 were observed in group II in which aplastic anemia was induced. In particular, a significant macrobiotic effect was observed in the group to which 1.56 mg/kg of the compound No. 1 was administered. These results suggest that the compound No. 1 would be effective in treating aplastic anemia.

TABLE 9

| | Survival rate on 30th day | |
|---|---|---|
| Group | survival animals/ total animals | average survival days ± S.D. |
| I | 10/10 | 30.0 ± 0 |
| II Dose of Cpd. No.1 | 2/10 | 15.9 ± 7.9 |
| none | | |
| 1.56 mg/kg | 7/10 | 24.7 ± 8.7* |
| 3.13 mg/kg | 6/10 | 22.4 ± 9.8 |

*p < 0.05;
Group I: irradiated with X-ray; and
Group II: irradiated with X-ray and incorporated with lymph node cells

TEST EXAMPLE 8

Therapeutic effect on adjuvant arthritis (a model of rheumatoid arthritis)

50 μl of an adjuvant obtained by suspending 12 mg/ml of M. butyricum in liquid paraffin was intracutaneously injected to the planta of a hind leg of a male Wistar Lewis rat aged six weeks. The volumes of both hind legs of the animal were determined 7, 14 and 21 days after the administration. The edematization rate was expressed in terms of the volume gain (%) with the volume of the leg on the previous day of the administration being defined as 100%. The test drug was intraperitoneally administered to the animal from the day of the administration of the adjuvant for 20 days once a day. However no drug was administered on the 4th, 11th and 18th days after the administration of the adjuvant. Aspirin was employed as a control drug. Table 10 shows the results.

TABLE 10

| Drug | Dose (mg/kg) | No. of examples | Edematization rate (%) 7th day | 14th day | 21st day |
|---|---|---|---|---|---|
| Leg treated with adjuvant | | | | | |
| physiological saline | | 10 | 99.6 ± 4.28 | 111.4 ± 4.89 | 123.6 ± 5.81 |
| compound (1) | 8 | 5 | 76.4 ± 3.28** | 76.9 ± 9.61** | 114.4 ± 10.70 |
| aspirin | 213 | 10 | 69.0 ± 3.14*** | 77.3 ± 4.06*** | 74.2 ± 3.97*** |
| Untreated leg | | | | | |
| physiological saline | | 10 | 2.6 ± 1.58 | 59.2 ± 4.87 | 85.5 ± 4.56 |
| compound (1) | 8 | 5 | 0.9 ± 1.80 | 2.2 ± 2.15*** | 20.6 ± 13.11*** |
| aspirin | 213 | 10 | 1.3 ± 1.01 | 44.3 ± 3.60* | 63.2 ± 4.04** |

Average ± S.D.,
*$P < 0.05$,
**$P < 0.01$,
***$P < 0.001$.

Table 10 shows that the compound (1) exhibits a remarkable effect of suppressing adjuvant arthritis when intraperitoneally administered in a dose of 8 mg/kg. This result suggests that this compound is effective in suppressing rheumatoid arthritis.

ADVANTAGES OF THE INVENTION

As is clear from the foregoing description, the compounds of the present invention have a relatively low toxicity ($LD_{50}$ between 12.5 and 50 mg/kg) and exhibit good immunosuppressive actions such as the inhibition of delayed-type hypersensitivity, the inhibition of the functions of T- and B-lymphocytes, and the inhibition of the production of antibodies against sheep red blood cells. The compounds of the present invention seem to have a different mechanism of action from the prior art immunosuppressants, and because of this fact, immunosuppressing agents having lower side effects may be prepared from the compounds of the present invention.

The following Examples are provided for further illustrations of the present invention.

EXAMPLE 1

Thirty parts by weight of a hydrochloride of compound No. 1 was mixed with purified water to make a total of 2,000 parts. The solution was passed through a Millipore filter of GS type for sterilization purposes. Two grams of the filtrate was put into 10-ml vials and freeze-dried to prepare injections each containing 30 mg of the hydrochloride of compound (1) per vial.

EXAMPLE 2

Granules

An intimate mixture of 50 parts by weight of a hydrochloride of compound (2), 600 parts of lactose, 330 parts of crystalline cellulose and 20 parts of hydroxypropyl cellulose was compacted with a Roller Compactor®, and ground into particles which were sieved to provide granules of a size between 16 and 60 mesh.

EXAMPLE 3

Tablets

A mixture of 30 parts by weight of a hydrochloride of compound (3), 120 parts of crystalline lactose, 147 parts of crystalline cellulose and 3 parts of magnesium stearate was processed with a V-type pelletizing machine to produce tablets each weighing 300 mg.

The following Reference Examples are given to show the methods of synthesizing the novel compounds in accordance with the present invention. In the Reference Examples, diz, TAD, and GP represent dibenzyloxycarbonyl, triazadecane and guanidinophenyl, respectively.

REFERENCE EXAMPLE 1

N-[4-(3-aminopropyl)aminobutyl]-2-[4-(p-guanidinophenyl)-butanamido]-(S)-2-hydroxymethylethanamide (Compound No. 7)

(1)

N-[4-(3-benzyloxycarbonylaminopropyl)benzyloxycarbonylaminobutyl]-2-[4-(p-guanidinophenyl)-butanamido]-(S)-2-benzyloxymethylethanamide 1.26 g (4.89 mmol) of brown crystalline 4-(4-GP)-butyrate hydrochloride was dissolved in 20 ml of dimethylformamide. To the ice-cooled solution, 0.68 g (5.87 mmol) of N-hydroxysuccinimide and 1.20 g (5.87 mmol) of N,N'-dicyclo-hexylcarbodiimide were added and the mixture was held overnight at room temperature. The precipitating N,N'-dicyclohexylurea was filtered off and the filtrate was immediately used in the subsequent reaction. 3.54 g (6.00 mmol) of a pale yellow oil of 10-(O-benzyl-L-seryl)-1,5-diz-1,5,10-TAD was dissolved in 30 ml of dimethylformamide. To the ice-cooled solution, 0.61 g (6.00 mmol) of triethylamine was added. After addition of the separately prepared dimethylformamide solution of the N-hydroxysuccinimide ester of 4-(4-GP)butyrate hydrochloride, the mixture was left to stand overnight at room temperature. The reaction mixture was concentrated under vacuum and the oily residue was dissolved in a mixture of 150 ml of ethyl acetate and 150 ml of chloroform. The solution was washed successively with 5% aqueous sodium carbonate, 0.5N HCl and saturated aqueous NaCl. The organic layer was dried over anhydrous sodium sulfate and the desiccator was filtered off. Upon concentration of the filtrate under vacuum, a pale yellow oil of the end compound was obtained in an amount of 4.10 g (yield: quantitative).

TLC (chloroform:methanol:17% aqueous ammonia=6:1.5:0.25 v/v).

Rf=0.16.

The 4-(4-GP)butyrate hydrochloride was synthesized by the following method.

1.60 g (8.93 mmol) of brown crystalline 4-(4-aminophenyl) butyric acid was dissolved in 40 ml of tetrahydrofuran. To the solution, 2.70 g (13.4 mmol) of a nitrate salt of 1-amidino-3,5-dimethylpyrazole and 2.19 g (17.0 mmol) of N,N-diisopropylethylamine were added, and the mixture was subjected to heating overnight under reflux. The precipitating crystal was recovered by filtration and washed successively with acetone, methanol and tetrahydrofuran. The dried brown crystal was suspended in 10 ml of distilled water and 1N HCl was added until the crystal dissolved completely. Following concentration to dryness under vacuum, the residue was washed twice, each time with ether and acetone, thereby producing 1.54 g of a brown crystal (yield: 67.0%). m.p. 157°–160° C.

(2)
N-[4-(3-aminopropyl)aminobutyl]-2-[4-(p-guanidinophenyl)butanamido]-(S)-2-hydroxymethylethanamide 4.06 g (4.89 mmol) of a pale yellow oil of N-[4-(3-benzyloxycarbonylaminopropyl)benzyloxycarbonylaminobutyl]-2-(7-guanidinophenyl)butanamido]-(S)-2-benzyloxymethylethanamide hydrochloride was dissolved in a mixture of methanol (50 ml) and acetic acid (30 ml). After addition of palladium black (0.4 g), the solution was heated to 55° C., at which temperature catalytic reduction was performed for 6 hours at atmospheric pressure. After completion of the reaction, the catalyst was filtered off, and the filtrate was concentrated under vacuum to obtain 2.80 g of an oily product. The oil was dissolved in 25 ml of 0.3M NaCl in 60% (v/v) aqueous methanol, and the solution was passed through a column of 350 ml of CM-Sephadex ® C-25 (Na+) that had been equilibrated with the same solvent.

The column was eluted by the gradient elution between 2,000 ml of 0.3M NaCl in 60% (v/v) aqueous methanol and 2,000 ml of 1M NaCl in 60% (v/v) aqueous methanol. The fractions containing the end compound were collected and concentrated to dryness under vacuum. Methanol was added to the residue and the insoluble NaCl was filtered off. The resulting oil was purified by the following procedure.

In order to remove the small amount of residual NaCl, the oil was dissolved in 5 ml of methanol, and the solution was passed through a column filled with 100 ml of Sephadex ® LH-20, followed by elution with methanol, collection of the active fractions and concentration thereof under vacuum. In order to remove the small amount of the still remaining impurities, the oil was dissolved in 5 ml of distilled water, and the solution was passed through a column filled with 80 ml of HP-20 ® (product of Mitsubishi Chemical Industries Limited), followed by elution with distilled water, collection of the active fractions and concentration thereof under vacuum. The resulting oil was dissolved in 5 ml of distilled water and the insoluble matter was filtered off. The filtrate was freeze-dried to produce 1.17 g of the end compound (yield: 44.0%).

TLC (n-propanol:pyridine:water:acetic acid=6:4:3:2 v/v).
Rf=0.34.
$[\alpha]_D^{19.5} -13.8°$ (C=1.17, $H_2O$).

REFERENCE EXAMPLE 2

N-[4-(3-aminopropyl)aminobutyl]-2-[4-(p-guanidinophenyl)butanamido]ethanamide (Compound No. 6)

(1) 10-(N,N-phthalylglycyl)-1,5-diz-1,5,10-TAD 12.4 g (30.0 mmol) of 1,5-diz-1,5,10-TAD was dissolved in 200 ml of tetrahydrofuran. To the ice-cooled solution, 4.90 ml (35.0 mmol) of triethylamine and 10.6 g (35.0 mmol) of an ester of phthalylglycine and N-hydroxysuccinimide were added, and the mixture was left overnight at room temperature.

The reaction mixture was concentrated to dryness under vacuum and the residue was dissolved n 1,200 ml of ethyl acetate. The ethyl acetate solution was washed successively with 5% aqueous sodium hydrogencarbonate, 0.5N HCl and saturated aqueous NaCl. The ethyl acetate layer was dried on anhydrous sodium sulfate, and the desiccator was filtered off whereas the filtrate was concentrated under vacuum. To the resulting residue, ethyl acetate and ethyl ether were added, and the resulting crystal was recovered by filtration and dried to give 14.6 g of the end compound (yield: 81.0%). m.p. 102°–104° C.

TLC (chloroform:methanol:acetic acid=95:5:3 v/v).
Rf=0.4.

(2) 10-glycyl-1,5-diz-1,5,10-TAD

To 14.4 g (24.0 mmol) of the 10-(N,N-phthalylglycyl)-1,5-diz-1,5,10-TAD, 370 ml of ethanol and 6.00 g (120 mmol) of hydrazine hydrate were added, and the mixture was refluxed for 2 hours. After completion of the reaction, the insoluble matter was filtered off and the filtrate was concentrated under vacuum. The resulting oil was dissolved in 300 ml of ethyl acetate and the solution was washed successively with 5% aqueous sodium hydrogencarbonate and distilled water. The ethyl acetate layer was dried on anhydrous sodium sulfate. After filtering off the desiccator, the filtrate was concentrated under vacuum to give 12.5 g of the end compound as an oil (yield: quantitative).

TLC (chloroform:methanol:acetic acid=95:5:3 v/v).
Rf=0.10.

(3)
N-[4-(3-benzyloxycarbonylaminopropyl)benzyloxycarbonylaminobutyl]-2-[4-(p-guanidinophenyl)-butanamido]ethanamide 1.56 g (6.05 mmol) of a brown crystalline 4-(4-GP)-butyrate hydrochloride was dissolved in 20 ml of dimethylformamide. To the ice-cooled solution, 0.84 g (7.26 mmol) of N-hydroxysuccinimide and 1.50 g (7.26 mmol) of N,N'-dicyclohexylcarbodiimide were added, and the mixture was held at room temperature overnight. The precipitating N,N'-dicyclohexylurea was filtered off and the filtrate was immediately used in the subsequent reaction.

2.59 g (5.5 mmol) of a pale yellow oil of 10-glycyl-1,5-diz-1,5,10-TAD was dissolved in 30 ml of dimethylformamide. To the ice-cooled solution, 0.61 g (6.05 mmol) of triethylamine was added. After addition of the separately prepared dimethyl formamide solution of the ester of 4-(4-GP)butyrate hydrochloride and N-hydroxysuccinimide, the mixture was held at room temperature overnight. The reaction mixture was concentrated under vacuum and the resulting oily residue was dissolved in a mixture of ethyl acetate (300 ml) and ethanol (60 ml). The solution was washed successively with 5% phosphoric acid, 5% aqueous sodium carbonate and saturated aqueous NaCl. Any oil that came out of the solution during washing was dissolved by addition of a small amount of ethanol. The organic layer was dried on anhydrous sodium sulfate. After filtering off the desiccator, the filtrate was concentrated under vacuum to give 3.30 g of the end compound as a pale yellow oil (yield: 89.1%).

TLC (chloroform:methanol:17% aqueous ammonium=6:3.5:1 v/v).
Rf=0.59.

(4)
N-[4-(3-aminopropyl)aminobutyl]-2-[4-(p-guanidinophenyl)butanamido]ethanamide 3.30 g (4.90 mmol) of the pale yellow oil prepared in (3) was dissolved in 40 ml of acetic acid. To the solution, 0.3 g of palladium black was added and the mixture was heated to 50° C., at which temperature catalytic reduction was conducted for 10 hours at atmospheric pressure. After completion of the reaction, the catalyst was filtered off and the filtrate was concentrated under vacuum to give 2.10 g of an oil.

The oil was dissolved in 10 ml of distilled water and the solution was passed through a column packed with 220 ml of CM-Sephadex® C-25 (Na+). The column was then eluted by the gradient elution between 1,100 ml of distilled water and 1,100 ml of an aqueous solution of 1.0M NaCl. The fractions containing the end compound were collected and concentrated to dryness under vacuum. Methanol was added to the dry product and the insoluble NaCl was filtered off.

Purification by the method used in Reference Example 1 gave 0.89 g of the end compound (yield: 35.3%).

TLC (n-propanol:pyridine:water:acetic acid=6:4:3:2 v/v).
Rf=0.26.

REFERENCE EXAMPLE 3

N-[4-(3-aminopropyl)aminobutyl]-2-[3-(p-guanidinomethylphenyl)propanamido]-(S)-2-hydroxymethylethanamide (Compound No. 8)

(1)
N-[4-(3-benzyloxycarbonylaminopropyl)benzyloxycarbonylaminobutyl]-2-[3-(p-guanidinomethylphenyl)-propanamido]-(S)-2-benzyloxymethylethanamide One gram (4.52 mmol) of a pale yellow crystal of 3-(4-guanidinomethylphenyl)propionic acid was added in 4-5 small portions to 3 ml of ice-cooled thionyl chloride. Thereafter, the mixture was subjected to reaction for 15 minutes under cooling with ice. The reaction mixture was then concentrated to dryness under vacuum. Two grams (3.38 mmol) of 10-(0-benzyl-L-seryl)-1,5-diz-1,5,10-TAD was dissolved in 10 ml of dimethylformamide. To the ice-cooled solution, 0.92 g (9.04 mmol) of triethylamine was added. After addition of a solution in 4 ml of dimethylformamide of the separately prepared 3-(4-GP)propionyl chloride hydrochloride, the mixture was subjected to reaction for 30 minutes under cooling with ice.

The reaction mixture was concentrated under vacuum and the oily residue was dissolved in a mixture of ethyl acetate (300 ml) and ethanol (50 ml). The solution was washed successively with 5% phosphoric acid, 5% aqueous sodium carbonate and saturated aqueous NaCl. Any oil that came out of the solution during the washing was dissolved by addition of a small amount of ethanol. The organic layer was dried on anhydrous sodium sulfate. After filtering off the desiccator, the filtrate was concentrated under vacuum to give 2.67 g of the end compound as a pale yellow oil (yield: quantitative).

TLC (chloroform:methanol:17% aqueous ammonia=6:1.5:0.25 v/v).
Rf=0.27

The 3-(4-quanidinomethylphenyl)propionic acid used as the starting material was synthesized by the following procedure.

(a) methyl ester of 3-(4-aminomethylphenyl)propionic acid 4.30 g (22.97 mmol) of a white crystal of methyl 3-(4-cyanophenyl)propenate was dissolved in 350 ml of ammonia-saturated methanol. To the solution, 3 g of Raney nickel was added and 60 atmospheres of hydrogen was supplied for 2 hours at room temperature. After completion of the reaction, the catalyst was filtered off and the filtrate was concentrated under vacuum to give 4.02 g of an oil (yield: 90.54%).

TLC (chloroform:methanol=10:1 v/v).
Rf=0.16.

(b) 3-(4-guanidinophenyl)propionic acid 3.70 g (19.14 mmol) of the oily methyl ester of 3-(4-aminomethylphenyl)propionic acid was dissolved in 150 ml of tetrahydrofuran. To the solution were added 5.80 g (28.71 mmol) of 1-amidino-3,5-dimethylpyrazole nitrate and 4.70 g (36.37 mmol) of N,N-diisopropylethylamine, and the mixture was heated overnight under reflux. The reaction mixture was concentrated under vacuum to give an oil. This oil was reacted with 70 ml of 5% HCl for 3 hours under reflux. The reaction mixture was passed through a filter and the filtrate was ice-cooled. The pH of the filtrate was adjusted to 6.4 by addition of 10% aqueous NaOH. The so adjusted filtrate was stirred for 30 minutes under ice-cooling. The precipitating crystal was recovered by filtration and washed successively with distilled water and tetrahydrofuran. Upon drying, 2.85 g of a pale yellow crystal was obtained (yield: 67.4%). m.p.≧300° C.

(2)
N-[4-(3-aminopropyl)aminobutyl]-2-[3-(p-guanidinomethylphenyl)propanamido]-(S)-2-hydroxymethylethanamide 2.60 g (3.27 mmol) of the pale yellow oil obtained in (1) was dissolved in a mixture of methanol (40 ml) and acetic acid (30 ml). After addition of palladium black (0.20 g), the solution was heated to 55° C., at which temperature catalytic reduction was conducted for 5 hours at one atmosphere. After completion of the reaction, the catalyst was filtered off and the filtrate was concentrated under vacuum to give 1.8 g of an oil. The oil was dissolved in 10 ml of distilled water, and the solution was passed through a column packed with 220 ml of CM-Sephadex® C-25 (Na+), followed by elution by the gradient elution between 1,100 ml of distilled water and 1,100 ml of an aqueous solution of 1.2M NaCl. The fractions containing the end compound were collected and concentrated to dryness under vacuum. Methanol was added to the dry product and the insoluble NaCl was filtered off.

By purifying the oil in accordance with the method used in Reference Example 2, the end compound was obtained in an amount of 0.84 g (yield: 47.2%).

Rf=0.25.

[α]$_D^{19.5}$ −24.8° (C=1.0, H$_2$O).

REFERENCE EXAMPLE 4

N-[4-(3-aminopropyl)aminobutyl]-2-[5-(p-guanidinophenyl)pentanamino]-(S)-2-hydroxymethylethanamide (Compound No. 9)

(1)

N-[4-(3-benzyloxycarbonylaminopropyl)benzyloxycarbonylaminobutyl]-2-[5-(p-guanidinophenyl)pentanamido]-(S)-2-benzyoxymethylethanamide 0.80 g (3.40 mmol) of a pale yellow crystal of 5-(4-GP) pentanoic acid and 1.80 g (3.05 mmol) of a pale yellow oil of 10-(0-benzyl-L-seryl)-1,5-diz-1,5,10-TAD were treated as in Reference Example 3 to produce 2.42 g of the end compound as a pale yellow oil (yield: quantitative).

TLC (chloroform:methanol:17% aqueous ammonia=6:1.5:0.25 v/v).

Rf=0.38.

The 5-(4-GP)pentanoic acid was synthesized by the following method.

7.42 g (35.80 mmol) of an oil of methyl 5-(4-aminophenyl)pentanoate was treated as in Reference Example 3, whereupon 3.72 g of the end compound was obtained as a pale yellow crystal (yield: 44.1%). m.p. 254°–256° C.

(2)

N-[4-(3-aminopropyl)aminobutyl]-2-[5-(p-guanidinophenyl)pentanamido]-(S)-2-hydroxymethylethanamide 2.42 g (3.00 mmol) of the pale yellow oil prepared in (1) was treated as in Reference Example 3 to give 0.69 g of the end compound (yield: 41.1%).

TLC (chloroform:methanol:17% aqueous ammonia=4:4:2 v/v).

Rf=0.50.

We claim:

1. A method for suppressing the functions and proliferations of B- and T-lymphocytes in a warm-blooded animal having a disease caused by an abnormally enhanced immunity which method comprises administering a spergualin-related compound represented by the following formula $$NH_2-\overset{\overset{NH}{\|}}{C}-NH-R_1-R_2-CONH-R_3-CONH-(CH_2)_4-NH-(CH_2)_3-NH$$

wherein R$_1$ is —(CH$_2$)$_4$—, —(CH$_2$)$_6$—,

—⟨phenyl⟩—CH$_2$—, —⟨phenyl⟩—(CH$_2$)$_2$— of

—CH$_2$—⟨phenyl⟩—;

R$_2$ is —(CH$_2$)$_2$— or —CH=CH—; and R$_3$ is

—CH—, —CH—, —CH$_2$— or —CH—
 |         |                    |
 OH       OCH$_3$              CH$_2$OH or pharmacologically acceptable salts thereof in an effective amount to said warm-blood animal.

2. The method according to claim 1, in which (a) R$_1$ is —(CH$_2$)$_4$— or —(CH$_2$)$_6$—, R$_2$ is —(CH$_2$)$_2$— and R$_3$ is —CH—, —CH—, —CH$_2$— or —$\overset{(S)}{CH}$— , or (b)
 |         |                    |
 OH       OCH$_3$              CH$_2$OH R$_1$ is —⟨phenyl⟩—CH$_2$—, —CH$_2$—⟨phenyl⟩— or —⟨phenyl⟩—(CH$_2$)$_2$—, R$_2$ is —(CH$_2$)$_2$— and R$_3$ is —CH$_2$— or

—CH— ,
 |
 CH$_2$OH or (c) R$_1$ is —(CH$_2$)$_4$— or —(CH$_2$)$_6$—, R$_2$ is —CH=CH— (trans) and R$_3$ is —CH— or —CH—.
 |         |
 OH       OCH$_3$ 3. The method according to claim 1 in which the spergualin-related compound is N-[4-(3-aminopropyl) aminobutyl]-2-(7-guanidinoheptanamide)-2-hydroxyethanamide.

4. The method according to claim 1 in which the spergualin-related compound is N-[4-(3-aminopropyl)aminobutyl]-2-[4-(p-guanidinophenyl) butanamide]ethanamide.

5. The method according to claim 1 in which the spergualin-related compounds is N-[4-(3-aminopropyl)aminobutyl]-2-[4-(p-guanidinophenyl) butanamide]-(S)-2-hydroxymethylethanamide.

* * * * *